United States Patent
Wang et al.

(10) Patent No.: US 10,266,512 B2
(45) Date of Patent: Apr. 23, 2019

(54) PROCESSES FOR PREPARING HETEROATOM CONTAINING CYCLIC DIMERS

(71) Applicant: Novus International, Inc., St. Charles, MO (US)

(72) Inventors: Xiaojun Wang, St. Charles, MO (US); Mark A. Hochwalt, St. Charles, MO (US); Graciela B. Arhancet, St. Charles, MO (US)

(73) Assignee: Novus International, Inc., St. Charles, MO (US)

( * ) Notice: Subject to any disclaimer, the term of this patent is extended or adjusted under 35 U.S.C. 154(b) by 0 days.

(21) Appl. No.: 15/673,638

(22) Filed: Aug. 10, 2017

(65) Prior Publication Data

US 2019/0047975 A1    Feb. 14, 2019

(51) Int. Cl.
    *C07D 319/12*         (2006.01)

(52) U.S. Cl.
    CPC ................... *C07D 319/12* (2013.01)

(58) Field of Classification Search
    CPC .................................................. C07D 319/12
    See application file for complete search history.

(56) References Cited

U.S. PATENT DOCUMENTS

| | | | |
|---|---|---|---|
| 4,033,938 A | 7/1977 | Augurt et al. | |
| 5,274,073 A | 12/1993 | Gruber et al. | |
| 5,288,881 A | 2/1994 | Drysdale et al. | |
| 5,310,599 A | 5/1994 | Ford | |
| 5,856,523 A | 1/1999 | Miao et al. | |
| 5,900,491 A | 5/1999 | Kurashima et al. | |
| 6,107,496 A | 8/2000 | Osterholt et al. | |
| 6,452,051 B1 | 9/2002 | Eyal | |
| 6,984,293 B2 | 1/2006 | Cockrem et al. | |
| 7,781,600 B2 | 8/2010 | Ogawa et al. | |
| 8,383,835 B2 | 2/2013 | Wajc et al. | |
| 8,430,948 B2 | 4/2013 | Hagen et al. | |
| 8,759,545 B2 | 6/2014 | Hong et al. | |
| 9,011,832 B2 * | 4/2015 | Arhancet ............... C08G 67/00 424/78.38 |
| 9,512,100 B2 | 12/2016 | Ikeyama et al. | |
| 9,539,561 B2 | 1/2017 | Hwang et al. | |
| 9,573,924 B2 | 2/2017 | Sels et al. | |
| 2006/0252134 A1 | 11/2006 | Lorbert et al. | |
| 2010/0098801 A1 | 4/2010 | Kobler et al. | |
| 2010/0121024 A1 | 5/2010 | Magnet et al. | |
| 2012/0035341 A1 | 2/2012 | Diehl et al. | |
| 2013/0267716 A1 | 10/2013 | Hong et al. | |
| 2015/0191444 A1 | 7/2015 | Arhancet et al. | |
| 2015/0329516 A1 | 11/2015 | Hagen et al. | |
| 2016/0024043 A1 | 1/2016 | Stepanski et al. | |
| 2016/0039782 A1 | 2/2016 | Li et al. | |
| 2018/0022867 A1 | 1/2018 | Takahashi | |

FOREIGN PATENT DOCUMENTS

WO      03/82836 A1    10/2003

OTHER PUBLICATIONS

Abell et al., "Synthesis of a [1,4]dioxane-2,5-dione based-peptidomimetic scaffold," ARKIVOC, 2006 (iii), pp. 72-76.
Gerhardt et al., "Functional Lactide Monomers: Methodology and Polymerization," Biomacromolecules, 2006, pp. 1735-1742, vol. 7, No. 6.
Gu et al., "Synthesis and evaluation of a biodegradable material with cell recognition motives," Carbohydrate Polymers, 2008, pp. 572-578, vol. 74.
Hayashi et al., "Analysis of Amide Bond Formation with an α-Hydroxy-β-amino Acid Derivative, 3-Amino-2-hydroxy-4-phenylbutanoic Acid, as an Acyl Component: Byproduction of Homobislactone," J. Org. Chem., 2001, pp. 5537-5544, vol. 66, No. 16.
John et al., "Synthesis and Modification of New Biodegradable Copolymers: Serine/Glycolic acid Based Copolymers," New Biodegradable Copolymers, 1997, pp. 1901-1907.
Leemhuis et al., "A Versatile Route to Functionalized Dilactones as Monomers for the Synthesis of Poly(α-hydroxy) Acids," Eur. J. Org. Chem., 2003, pp. 3344-3349.
International Search Report and Written Opinion from related International Application No. PCT/US2017/047114, dated Dec. 4, 2017; 17 pgs.

* cited by examiner

*Primary Examiner* — D Margaret M Seaman

(74) *Attorney, Agent, or Firm* — Polsinelli PC

(57) ABSTRACT

Processes for preparing heteroatom containing cyclic dimers that result in increased production efficiency and reduced waste production.

28 Claims, 1 Drawing Sheet

PROCESSES FOR PREPARING HETEROATOM CONTAINING CYCLIC DIMERS

FIELD

The invention relates to improved and efficient processes for preparing heteroatom containing cyclic dimers.

BACKGROUND

Cyclic dimers of alpha hydroxy acids are useful for a variety of applications. For example, lactic acid cyclic dimers, also called lactides, provide an important route to poly(lactic acid). Similarly, cyclic dimers of methionine hydroxy analogs, as described in U.S. Pat. No. 9,011,832, have utility as plasticizers, wetting agents, feed additives, and the like, as well as starting materials for polymers and copolymers comprising heteroatom containing side chains as described in U.S. Pat. No. 9,284,924. Current processes for preparing cyclic dimers of methionine hydroxy analogs, however, have low yields, high capital costs, and large waste streams. Thus, there is a need for improved processes for preparing heteroatom containing cyclic dimers.

SUMMARY

Among the various aspects of the present disclosure is provided a process for preparing a compound of Formula (III) by contacting a compound of Formula (I) with a compound of Formula (II). The process comprises (a) forming a reaction mixture comprising a nonpolar solvent and the compounds of Formula (I) and Formula (II), wherein the reaction mixture comprises a weight-to-weight ratio of the nonpolar solvent to the compounds of Formula (I) and Formula (II) of less than 20:1; (b) heating the reaction mixture in the presence of at least one acid catalyst under dehydration to form the compound of Formula (III); (c) adding water to the reaction mixture after step (b) to form an aqueous phase and an organic phase comprising the compound of Formula (III), wherein the aqueous phase comprises oligomers of the compounds of Formula (I) and Formula (II) and a residual level of the compound of Formula (III); (d) extracting the aqueous phase with the nonpolar solvent to form another organic phase comprising the compound of Formula (III), wherein the nonpolar solvent used in step (b) is the same nonpolar solvent as that used in step (a); and (e) combining the organic phases comprising the compound of Formula (III) and isolating the compound of Formula (III) from the organic phases. The compounds of Formulas (III), (II), and (I) have the following structures:

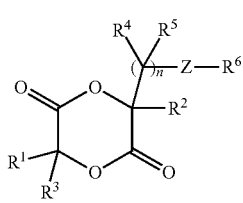

(III)

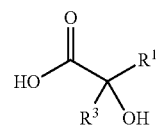

(I)

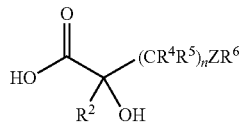

(II)

wherein:
R$^1$, R$^2$, R$^3$, R$^4$, and R$^5$ independently are hydrogen, alkyl, or substituted alkyl;
R$^6$ is hydrogen, alkyl, substituted alkyl, aryl, or substituted aryl;
Z is sulfur, sulfone, sulfoxide, or selenium; and
n is an integer from 1 to 10.
Other aspects and iterations of the disclosure are detailed below.

DETAILED DESCRIPTION

Figure 1:
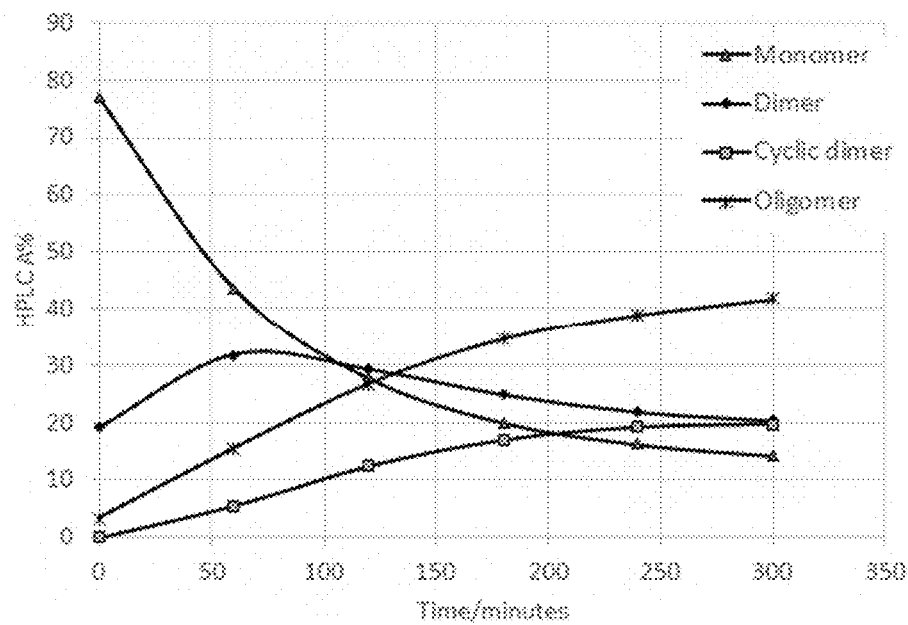
FIG. 1 shows a typical reaction kinetic curve. The reaction components are plotted as a function of time.

The present disclosure provides improved processes for preparing heteroatom containing cyclic dimers from heteroatom containing alpha hydroxy acid monomers. The processes disclosed herein improve production efficiency and reduce waste generation by using a single nonpolar solvent during the reaction and extraction steps of the process. Production efficiency is also increased by converting by-product oligomers into the starting monomers and recycling them back to the initial reaction step of the process.

(I) Processes for Preparing Cyclic Dimer Compounds

Provided herein are processes for preparing cyclic dimers by cyclizing monomeric compounds. The processes comprise at least four steps: (1) a reaction step in which the monomeric compounds are heated in the presence of an acid catalyst and a nonpolar solvent to form the cyclic dimer compound; (2) a phase partitioning step in which water is added to the reaction mixture to form an organic phase predominantly comprising the cyclic dimer compound and an aqueous phase predominantly comprising the starting monomers and byproduct oligomeric compounds; (3) an extraction step in which the aqueous phase is extracted with the nonpolar solvent to recover any residual cyclic dimer compound; and (4) a crystallization step in which the cyclic dimer compound is isolated form the organic phase(s). In some embodiments, the process further comprises (5) a recycle step in which byproduct oligomeric compounds in the aqueous phase are hydrolyzed to monomeric compounds that are recycled back to the reaction step of the process.

(a) Monomeric and Cyclic Dimer Compounds

The processes comprise contacting monomeric compounds of Formulas (I) and (II) to form a cyclic dimer compound of Formula (III), the structures of which are shown below.

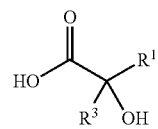

(I)

-continued

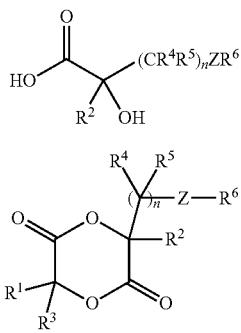

(II)

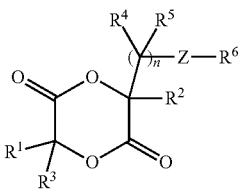

(III)

wherein:
$R^1$, $R^2$, $R^3$, $R^4$, $R^5$, and $R^6$ independently are hydrogen, hydrocarbyl, or substituted hydrocarbyl;
Z is sulfur, sulfone, sulfoxide, or selenium; and
n is an integer from 1 to 10.

Each of $R^1$, $R^2$, $R^3$, $R^4$, $R^5$, and $R^6$ may be chosen from hydrogen, hydrocarbyl, or substituted hydrocarbyl. In various embodiments, the hydrocarbyl may be, but is not limited to, alkyl, cycloalkyl, alkenyl, alkenoxy, aryl, or alkylaryl. Substituted hydrocarbyl may be, without limit, arylalkoxyl, alkoxy, alkoxycarbonyl, carbonyl, acyl, acyloxy, sulfidyl, sulfoxyl, sulfonyl, selenyl, sulfonyl halide, sulfonyl ester, carboxyl, carboxylic acid, hydroxyalkyl, alkyl halide, alkyl amine, alkyl amide, substituted alkyl amine, or alkyl amide. In certain embodiments, $R^1$, $R^2$, $R^3$, $R^4$, $R^5$, and $R^6$ may be chosen from hydrogen, alkyl, aryl, alkylaryl, substituted alkyl, substituted aryl, or substituted alkylaryl. In other embodiments, $R^2$, $R^3$, $R^4$, and $R^5$ independently may be hydrogen, alkyl, or substituted alkyl, and $R^6$ may be hydrogen, alkyl, substituted alkyl, aryl, or substituted aryl. In certain aspects, $R^2$, $R^3$, $R^4$, and $R^5$ independently may be hydrogen or $C_1$-$C_6$ alkyl. In other aspects, one or more of $R^2$, $R^3$, $R^4$, and $R^5$ may be hydrogen. In specific embodiments, each of $R^2$, $R^3$, $R^4$, and $R^5$ may be hydrogen.

In certain embodiments, $R^1$ may be hydrogen, alkyl, substituted alkyl, aryl, substituted aryl, alkylaryl, or substituted alkylaryl. In some instances, $R^1$ may be $C_1$-$C_6$ alkyl, such as methyl, ethyl, propyl, isopropyl, cyclopropyl, isobutyl, butyl, sec-butyl, tert-butyl, cyclobutyl, pentyl, cyclopentyl, hexyl, cyclohexyl, or a $C_1$-$C_6$ alkyl substituted with a sulfur, sulfoxide, sulfone, or selenium group. In other instances, $R^1$ may be phenyl, benzyl, substituted phenyl, or substituted benzyl. In particular embodiments, $R^1$ may be $(CR^8R^9)_mYR^{10}$, wherein $R^8$, $R^9$, and $R^{10}$ independently may be hydrogen, hydrocarbyl, or substituted hydrocarbyl, Y may be sulfur, sulfone, sulfoxide, or selenium, and m may be an integer from 1 to 10.

In various embodiments, $R^6$ may be hydrogen, hydrocarbyl, or substituted hydrocarbyl. In some aspects, $R^6$ may be hydrogen, alkyl, substituted alkyl, aryl, or substituted aryl. In some instances, $R^6$ may be $C_1$-$C_6$ alkyl, such as methyl, ethyl, propyl, isopropyl, cyclopropyl, isobutyl, butyl, sec-butyl, tert-butyl, cyclobutyl, pentyl, cyclopentyl, hexyl, cyclohexyl. In other instances, $R^6$ may be phenyl, benzyl, substituted phenyl, or substituted benzyl. In specific embodiments, $R^6$ may be methyl.

In general, n ranges from 1 to 10. In some embodiments, n may be 1, 2, 3, 4, 5, 6, 7, 8, 9, or 10. In specific embodiments, n may be 1, 2, or 3.

In certain embodiments, Z may be selenium or sulfur, including sulfoxide and sulfone groups. The selenium or sulfur atoms may be charged and/or be present in various oxidation states within the molecule. In embodiments in which Z carries a charge, the compound may further comprise a counter ion including, but not limited to, lithium, sodium, potassium, calcium, magnesium, and the like.

In some embodiments, $R^1$, $R^2$, $R^3$, $R^4$, and $R^5$ independently may be hydrogen, alkyl, or substituted alkyl, and $R^6$ may be hydrogen, alkyl, substituted alkyl, aryl, or substituted aryl. In other embodiments, $R^1$ may be hydrogen, alkyl, or substituted alkyl, each of $R^2$, $R^3$, $R^4$, and $R^5$ may be hydrogen, $R^6$ may be methyl, n may be 2, and Z may be sulfur. In other embodiments, $R^1$ may be hydrogen, alkyl, or substituted alkyl, each of $R^2$, $R^3$, $R^4$, and $R^5$ may be hydrogen, $R^6$ may be methyl, n may be 2, and Z may be selenium.

In still other embodiments, the compound of Formula (I) may be a compound of Formula (Ia) and the compound of Formula (III) may be a compound of Formula (IIIa), as shown below

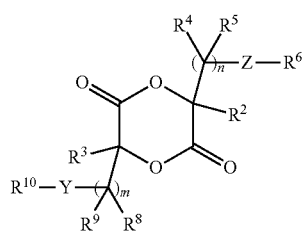

(Ia)

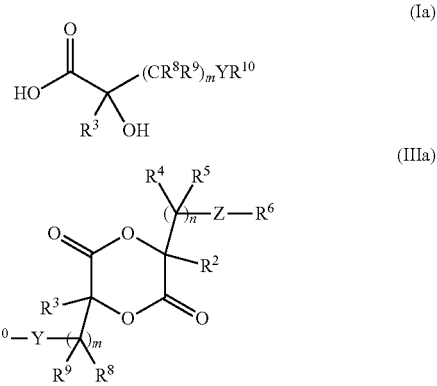

(IIIa)

wherein:
$R^2$, $R^3$, $R^4$, $R^5$, $R^6$, Z, and n are as described above for the compounds of Formulas (I), (II), and (III);
$R^8$, $R^9$, and $R^{10}$ independently are hydrogen, hydrocarbyl, or substituted hydrocarbyl;
Y is sulfur, sulfone, sulfoxide, or selenium; and
m is an integer from 1 to 10.

Each of $R^8$, $R^9$, and $R^{10}$ may be hydrogen, hydrocarbyl, or substituted hydrocarbyl. The hydrocarbyl may be, without limit, alkyl, cycloalkyl, alkenyl, alkenoxy, aryl, or alkylaryl. The substituted hydrocarbyl may be, without limit, arylalkoxyl, alkoxy, alkoxycarbonyl, carbonyl, acyl, acyloxy, sulfonyl, sulfonyl halide, sulfonyl ester, carboxyl, carboxylic acid, hydroxyalkyl, alkyl halide, alkyl amine, alkyl amide, substituted alkyl amine, or alkyl amide. In certain embodiments, $R^8$, $R^9$, and $R^{10}$ independently may be hydrogen, alkyl, aryl, alkylaryl, substituted alkyl, substituted aryl, and substituted alkylaryl. In other embodiments, $R^8$ and $R^9$ independently may be hydrogen, alkyl, or substituted alkyl, and $R^{10}$ may be hydrogen, alkyl, substituted alkyl, aryl, or substituted aryl. In certain aspects, $R^8$, $R^9$, and $R^{10}$ independently may be hydrogen or $C_1$-$C_6$ alkyl. In other aspects, one or more of $R^8$, $R^9$, and $R^{10}$ may be hydrogen. In a specific embodiment, $R^8$ and $R^9$ may be hydrogen.

In various embodiments, $R^{10}$ may be hydrogen, hydrocarbyl, or substituted hydrocarbyl. In some aspects, $R^{10}$ may be hydrogen, alkyl, substituted alkyl, aryl, or substituted aryl. In some instances, $R^{10}$ may be $C_1$-$C_6$ alkyl, such as methyl, ethyl, propyl, isopropyl, cyclopropyl, isobutyl, butyl, sec-butyl, tert-butyl, cyclobutyl, pentyl, cyclopentyl, hexyl, cyclohexyl. In other instances, $R^{10}$ may be phenyl, benzyl, substituted phenyl, or substituted benzyl. In specific embodiments, $R^{10}$ may be methyl.

In general, m ranges from 1 to 10. In some embodiments, m may be 1, 2, 3, 4, 5, 6, 7, 8, 9, or 10. In specific embodiments, m may be 1, 2, or 3.

In certain embodiments, Y may be selenium or sulfur, including sulfoxide and sulfone groups. The selenium or sulfur atoms may be charged and/or be present in various oxidation states within the molecule. In embodiments in which Y carries a charge, the compound may further comprise a counter ion including, but not limited to lithium, sodium, potassium, calcium, magnesium, and the like.

In some embodiments, $R^2$, $R^3$, $R^4$, $R^5$, $R^8$, and $R^9$ independently may be hydrogen, alkyl, or substituted alkyl, and $R^6$ and $R^{10}$ independently may be hydrogen, alkyl, substituted alkyl, aryl, or substituted aryl. In certain embodiments, each of $R^2$, $R^3$, $R^4$, $R^5$, $R^8$, and $R^9$ may be hydrogen, $R^6$ and $R^{10}$ independently may be $C_1$-$C_6$ alkyl, and n and m independently may be 1, 2, or 3. In additional embodiments each of $R^2$, $R^3$, $R^4$, $R^5$, $R^8$, and $R^9$ may be hydrogen, each of $R^6$ and $R^{10}$ may be methyl, each of n and m may be 2, and each of Z and Y may be sulfur or each of Z and Y may be selenium.

In specific embodiments, the compound of Formula (III) may be a compound of Formula (V) and each of the compounds of Formula (I) and Formula (II) may be a compound of Formula (IV), as shown below.

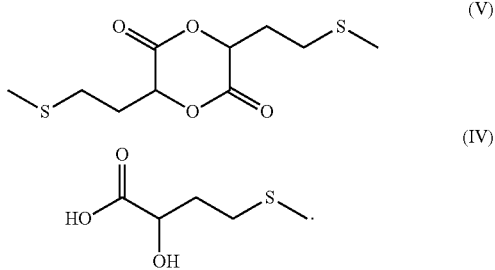

In some aspects, the compounds of Formulas (I), (Ia), (II), (III), (IIIa), (IV), and (V) comprise one or more chiral centers. Each chiral center may have an R or an S configuration. For example, in compounds comprising two chiral carbons, the configuration may be RR, RS, SR, or SS, in compounds comprising three chiral carbons, the configuration may be RRR, RRS, RSR, RSS, SRR, SRS, SSR, or SSS, etc.

(b) Reaction Step

The first step of the process comprises a reaction in which a compound of Formula (I) is contacted with a compound of Formula (II) in the presence of an acid catalyst and a nonpolar solvent, thereby forming the compound of Formula (III).

The reaction step commences with the formation of a reaction mixture in a reaction chamber. In general, the two compounds of Formulas (I) and (II) are provided to the reaction chamber in an approximately equal molar ratio. In some embodiments, the compound of Formula (I) may be provided in a molar ratio with respect to the compound of Formula (II) of about 0.2:1, about 0.25:1; about 0.33:1, about 0.5:1, about 1:1, about 2:1, about 3:1, about 2:1, about 4:1, or about 5:1. In specific embodiments, the molar ratio of the compound of Formula (I) to the compound of Formula (II) may range from about 0.9:1.1 to about 1.1:0.9, or the molar ratio may be about 1:1.

The reaction mixture also comprises a nonpolar solvent. Non-limiting examples of suitable nonpolar solvents include anisole, benzene, butyl acetate, chlorobenzene, chloroform, chloromethane, cyclohexane, dichloromethane, dichloroethane, di-tert-butyl ether, dimethyl ether, diethylene glycol, diethyl ether, diglyme, diisopropyl ether, ethyl tert-butyl ether, ethylene oxide, fluorobenzene, heptane, hexane, methyl tert-butyl ether, toluene, xylene, and combinations thereof. In certain embodiments, the nonpolar solvent may be anisole, benzene, chlorobenzene, di-tert-butyl ether, diethylene glycol, diglyme, diisopropyl ether, ethyl tert-butyl ether, fluorobenzene, methyl tert-butyl ether, toluene, xylene, or combinations thereof. In particular embodiments, the nonpolar solvent may be anisole, benzene, methyl tert-butyl ether, toluene, xylene, or combinations thereof. In specific embodiments, the nonpolar solvent may be toluene.

In general, the nonpolar solvent is provided to the reaction mixture in a weight-to-weight ratio of the nonpolar solvent to the monomer compounds of Formula (I) and Formula (II) of less than 20:1. In some embodiments, the weight-to-weight ratio of the nonpolar solvent to the compounds of Formula (I) and Formula (II) may be less than 15:1. In other embodiments, the weight-to-weight ratio of the nonpolar solvent to the compounds of Formula (I) and Formula (II) may be less than 10:1. In further embodiments, the weight-to-weight ratio of the nonpolar solvent to the compounds of Formula (I) and Formula (II) may be less than 5:1. In still other embodiments, the weight-to-weight ratio of the nonpolar solvent to the compounds of Formula (I) and Formula (II) may be less than 2.5:1. In yet other embodiments, the weight-to-weight ratio of the nonpolar solvent to the compounds of Formula (I) and Formula (II) may be less than 1.5:1. In other embodiments, the weight-to-weight ratio of the nonpolar solvent to the compounds of Formula (I) and Formula (II) may range from about 0.2:1 to about 20:1, or from about 0.5:1 to about 10:1. In yet additional embodiments, the weight-to-weight ratio of the nonpolar solvent to the compounds of Formula (I) and Formula (II) may range from about 0.7:1 to about 3:1, from about 0.8:1 to about 2.5:1, from about 1:1 to about 2:1, from about 1.2:1 to about 1.8:1, from about 1.4:1 to about 1.6:1, or about 1.5:1. In various embodiments, the weight-to-weight ratio of the nonpolar solvent to the compounds of Formula (I) and Formula (II) may be about 0.8:1, 0.9:1, 1:1, 1.1:1, 1.2:1, 1.3:3, 1.4:1, 1.5:1, 1.6:1, or 1.7:1.

The condensation reaction between the compounds of Formulas (I) and (II) is catalyzed by at least one acid catalyst. In general, the one or more acid catalysts may be chosen from organic acids, salts of organic acids, inorganic acids, salts of inorganic acids, solid resins, or combinations thereof. Suitable acid catalysts include, without limit, acetic acid, ammonium bisulfate, boric acid, hydrochloric acid, methanesulfonic acid, phosphoric acid, polyphosphoric acid, sodium bisulfate, sulfuric acid, trifluoroacetic acid, trifluoromethanesulfonic acid, toluenesulfonic acid (i.e., ortho-meta- and para-toluenesulfonic acid), xylenesulfonic acid, Dowex resins, Amberlyst resins, Zn dust, Sn based catalysts (e.g., Sn dust, tin oxide, tin(II) chloride, dibutyltin dilaurate, and stannous octoate), germanium dioxide, antimony trioxide, zinc oxide, iron(III) oxide, aluminum oxide, silicon dioxide, titanium dioxide, and combinations thereof. In certain embodiments, the at least one acid catalyst may be para-toluenesulfonic acid (pTSA), sulfuric acid, hydrochloric acid, sodium bisulfate, ammonium bisulfate, or combinations thereof. In some embodiments, the at least one acid catalyst may be pTSA, or a combination of pTSA and sulfuric acid.

The amount of acid catalyst added to the reaction mixture can and will vary. In general, the acid catalyst is present at a weight percent (wt %) of acid catalyst to the compounds of Formula (I) and Formula (II) of about 0.1 wt % to about 5 wt %. In certain embodiments, the amount of acid catalyst added to the reaction mixture may range from about 0.2 wt % to about 4.5 wt %, from about 0.4 wt % to about 4.0 wt %, from about 0.8 wt % to about 3.5 wt %, or from about 1.0 wt % to about 3.0 wt %. In embodiments in which the acid catalyst comprises pTSA, the amount of pTSA added to the reaction mixture may range from 0.6 wt % to about 2.0 wt %. In embodiments in which the acid catalyst comprises sulfuric acid, the amount of sulfuring acid added to the reaction mixture may range from 0.5 wt % to about 1.0 wt %. In embodiments in which the acid catalyst is a mixture of pTSA and sulfuric acid, the weight ratio of pTSA to sulfuric acid may range from about 1.2:1 to about 2:1. For example, the amount of acid catalyst added to the reaction mixture may range from 0.6-2.0 wt % of pTSA and 0.5-1.0 wt % of sulfuric acid. In certain specific embodiments, the amount of acid catalyst added to the reaction mixture may be about 0.6 wt % of pTSA and about 0.5 wt % of sulfuric acid.

The reaction mixture comprising the compounds of Formulas (I) and (II) and the at least one acid catalyst is heated to reflux, thereby forming the cyclic dimer compound of Formula (III), as well as linear dimers, trimers, and longer oligomers of the compounds of Formulas (I) and (II). In general, the temperature of the reaction may range from about 90° C. to about 150° C. In some embodiments, the temperature of the reaction may range from about 95° C. to about 130° C., from about 100° C. to about 125° C., or from about 105° C. to about 120° C. In specific embodiments, the temperature of the reaction may be about 110° C. to about 115° C.

The reaction is generally conducted under dehydration to promote condensation of the monomer compounds of Formulas (I) and (II). In certain embodiments, dehydration may be accomplished via distillation. For example, the reaction may be subjected to simple distillation, fractional distillation, extraction distillation, azeotropic distillation, steam distillation, vacuum distillation, extraction distillation using a Dean-Stark trap or another similar trap, azeotropic distillation using a Dean Stark or another similar trap, and the like. In specific embodiments, the reaction comprises heating with continuous removal of water using a condenser and a distillation adaptor or trap.

In some embodiments, the reaction may be conducted at atmospheric pressure. In other embodiments, the reaction may be conducted above or below atmospheric pressure. The reaction may be conducted under an inert atmosphere, e.g., under nitrogen, argon, or helium.

The duration of the reaction can and will vary. In general, the reaction is allowed to proceed for a sufficient period of time until the reaction is complete, as determined by means well known to those of skill in the art. In this context, the final reaction mixture contains significantly diminished amounts of the compounds of Formulas (I) and (II) and a significantly increased amount of the compound of Formula (III) compared to the amounts of each present at the beginning of the reaction. Generally, the duration of the reaction is adjusted to minimize formation of oligomers of the compounds of Formulas (I) and (II). In some embodiments, the reaction may be allowed to proceed for a period of time ranging from about 1 hour to about 24 hours, or from about 1 hour to about 10 hours. In another embodiment, the reaction may be allowed to proceed for a period of time ranging from about 5 hour to about 10 hours. In a preferred embodiment, the reaction may be allowed to proceed for a period for about 5 hours to about 7 hours.

The yield of the compound of Formula (III) can and will vary depending on the identity and relative ratios of the reactants, catalyst, etc. and the operating conditions. In general, the molar yield of the compound of Formula (III) will be at least about 5%. In various embodiments, the molar yield of the compound of Formula (III) may be at least about 10%, at least about 15%, at least about 20%, at least about 25%, at least about 30%, at least about 40%, or at least about 50%.

Upon completion of the reaction, the reaction mixture may be filtered to remove particulates and/or inorganic salts. Means for filtering are well known in the art.

In embodiments in which the starting materials contain a significant amount of water (e.g., greater than about 10 wt %), the reaction may be modified to include an initial step of reducing the water content of the reaction mixture prior to addition of the acid catalyst. For this, the reaction mixture comprising the monomer compounds of Formulas (I) and (I) and the nonpolar solvent may be subjected to a distillation process. Examples of suitable distillation processes are described above. The water content of the reaction mixture may be reduced to less than about 5%, less than about 4%, less than about 3%, less than about 2%, or less than about 1% by weight.

(c) Phase Partitioning Step

The processes disclosed herein further comprise a phase partitioning step. This step of the process comprises adding water to the final reaction mixture, thereby forming an organic phase and an aqueous phase. The majority of the cyclic dimer compound of Formula (III) is partitioned to the organic phase, and the majority of the starting monomers and byproduct oligomers of the compounds of Formulas (I) and (II) are partitioned to the aqueous phase.

The water added to the reaction mixture may be potable water, tap water, purified water, demineralized water, distilled water, or deionized water. In general, the amount of water added to the reaction mixture may range from about 2 wt % to about 20 wt %. In certain embodiments, the amount of water added to the reaction mixture may range from about 3 wt % to about 15 wt %, from about 4 wt % to about 10 wt %, from about 5 wt % to about 9 wt %, or from about 6 wt % to about 8 wt %.

After addition of the water, the water and the reaction mixture are mixed together to allow for the residual monomer and byproduct oligomers to be removed from the nonpolar solvent and dissolve in the water. In general, the mixing is performed at ambient temperature or a temperature less than ambient temperature. The mixing may be accomplished by agitating, stirring, rotating, or other means routine in the art and the rate of mixing may be adjusted to ensure complete mixing. In various embodiments, the duration of mixing may be less than about 60 minutes, less than about 30 minutes, or less than about 10 minutes. The mixture is allowed to separate into organic and aqueous layers, and the organic phase is removed from the aqueous phase using means routine in the art. The water may also be added to the reaction mixture in a continuous fashion in the ratios stated above and the mixture may be mixed using an inline mixer, educator, or any other suitable mixing device known in the art. The mixture then may be passed through a continuous extractor, mixer settler, or other suitable continuous contacting device designed for phase separation.

The resultant aqueous phase comprises the majority of the monomers and oligomers of compounds of Formulas (I) and (II), the acid catalyst, and residual levels of the cyclic dimer compound of Formula (III), whereas the organic phase comprises the majority of the cyclic dimer compound of Formula (III), the nonpolar solvent, and residual levels of the monomers and oligomers of the compounds of Formulas (I) and (II).

Generally, the aqueous phase may be extracted with nonpolar solvent to recover residual cyclic dimer compounds of Formula (III) thereby generating additional organic phases (which are combined with the original organic phase and subjected to crystallization as detailed below).

In some embodiments, however, the original organic phase may proceed to the crystallization step described below in section (I)(e) without the extraction step described below in section (I)(d). In situations in which the extraction step is eliminated, the yield of the compound of Formula (III) is reduced and the quality of the product is reduced in terms of purity, odor, and color.

(d) Extraction Step

The processes disclosed herein generally further comprise an extraction step during which the aqueous phase is subjected to one or more extractions with the nonpolar solvent to recover residual cyclic dimer compounds of Formula (III) present in aqueous phase.

Suitable nonpolar solvents are described above in section (I)(b). In general, the nonpolar solvent used during the extraction step is the same nonpolar solvent that is used during the reaction step of the process. In specific embodiments, the nonpolar solvent used during both steps is toluene.

The amount of nonpolar solvent that is contacted with the aqueous phase can and will vary. In general, the weight-to-weight ratio of the nonpolar solvent to the aqueous phase may range from about 1:1 to about 2:1. In some embodiments, the weight-to-weight ratio of nonpolar solvent to the aqueous phase may range from 1.1:1 to about 1.8:1, from about 1.2:1 to about 1.6:1, or from about 1.3:1 to about 1.5:1.

The aqueous phase and the nonpolar solvent generally are mixed either batchwise or in a continuous fashion essentially as described above. In general, the mixing is performed at ambient temperature or below ambient temperature. The mixture is allowed to separate into layers, thereby forming the aqueous phase and a second organic phase. The aqueous phase may be extracted a second time with the nonpolar solvent, essentially as described above, thereby forming the aqueous phase and a third organic phase. The aqueous phase may be extracted one, two, three, or more times with the nonpolar solvent, essentially as described above. Alternatively, the extraction may be a continuous process using a continuous extraction column or mixer settler as described above. Upon completion of the extraction step, the resultant aqueous phase may be subjected to a recycle process as detailed below in section (I)(f).

The one or more organic phases generated during the extraction step generally are mixed with the original organic phase formed during the phase partitioning step. The combined organic phases may be subjected to the crystallization step detailed below in section (I)(e).

Alternatively, the combined organic phases may be washed with water to reduce the levels of the monomers and oligomers of the compounds of Formulas (I) and (II) and the acid catalyst before the combined organic phases are subjected to the crystallization step detailed below in section (I)(e). The amount of water mixed with the combined organic phases may range from about 2 wt % to about 25 wt %, from about 4 wt % to about 20 wt %, or from about 6 wt % to about 12 wt %. The organic phases and the water may be mixed and separated as detailed above. The water-treated organic phases then may be subjected to the crystallization step as detailed below in section (I)(e). The resultant water wash may be combined with the aqueous phase from the extraction step, and the combined aqueous phases may be subjected to the recycle process described below in section (I)(f).

(e) Crystallization Step

The next step of the processes disclosed herein comprises isolating the cyclic dimer compound of Formula (III) by crystallizing the compound of Formula (III) from the combined organic phases.

The crystallization step of the process comprises concentrating the combined organic phases comprising the compound of Formula (III) by removing a majority of the nonpolar solvent, as well as any residual water. In some embodiments, the nonpolar solvent may be removed from the organic phases by distillation or evaporation at reduced pressure to form a concentrate comprising the compound of Formula (III). For example, the compound of Formula (III) may be concentrated in a rotary evaporator. In various embodiments, the concentration may occur at a pressure of less than about 500 millibar (mbar), less than about 250 mbar, less than about 100 mbar, less that about 50 mbar, less than about 25 mbar, less than about 10 mbar, or less than about 5 mbar. In general, the concentration occurs at a temperature of less than about 50° C., less than about 45° C., less than about 40° C., less than about 35° C., less than about 30°, less than about 25° C., or less than about 20° C. The concentration proceeds until the level of the nonpolar solvent remaining in the concentrate is less than about 10 wt %, less than about 8 wt %, less than about 6 wt %, less than about 4 wt %, less than about 3 wt %, less than about 2 wt %, or less than about 1 wt %.

The crystallization step of the process further comprises contacting the concentrate comprising the compound of Formula (III) with a solvent at reduced temperature to form crystals of the compound of Formula (III). Non-limiting examples of suitable solvents include isopropanol, methyl-t-butyl ether, benzene, butanol, ethanol, ethyl acetate, heptane, methanol, octane, tetrahydrofuran, toluene, and combinations thereof. In specific embodiments, the solvent may be isopropanol or methyl-t-butyl ether.

The weight-to-weight ratio of the solvent to the concentrate may range from about 0.5:1 to about 10:1, from about 0.8:1 to about 6:1, or from about 1:1 to about 3:1. In various embodiments, the weight-to-weight ratio of the solvent to the concentrate may be about 1:1, about 1.2:1, about 1.3:1, about 1.4:1, about 1.5:1, about 1.6:1, about 1.7:1, about 1.8:1, about 1.9:1, about 2:1, about 2.2:1, about 2.3:1, about 2.3:1, or about 2.5:1.

In general, the mixture comprising the solvent and the concentrate is mixed and heated to a temperature of less than about 50° C. to dissolve any solid material. In some embodiments, the mixture may be heated to a temperature of less than about 45° C., less than about 40° C., less than about 35° C., or less than about 30° C. to dissolve any solid material. The temperature of the mixture is then reduced to a temperature that allows crystallization to occur. A seed crystal may be added to the mixture to facilitate crystallization. In some embodiments, the mixture may be cooled to a temperature of less than about than about 30° C., less than about 25° C., less than about 15° C., or less than about 4° C. such that occurs. The crystallization temperature may be maintained from at least about 3 hours, at least about 6 hours, at least about 12 hours, or at least about 18 hours.

In some embodiments, the temperature of the mixture may be reduced using a nonlinear temperature gradient. For example, the mixture may be cooled to a temperature from about 25° C. to about 35° C., or about 28° C. to about 32° C., and the temperature may be maintained for up to about 0.5 hour, up to about 1 hour, up to 2 about hours, or up to about 3 hours. Then the mixture may be cooled to a temperature from about −10° C. to about 10° C., about −5° C. to about 5° C., or −2° C. to about 2° C. over a period of about 1.5 hours, about 2 hours, about 2.5 hours, or about 3 hours. In specific embodiments, the nonlinear temperature gradient comprises a first step at about 28° C. for about 3 hours and a second step of cooling to 0° over about 3 hours.

The crystallization product may be recovered by filtration or centrifugation. The filter cake may be re-slurried and washed with the solvent used during the crystallization process and re-filtered. The solvent may be cooled to about 10° C., about 5° C., or about 0° C. prior to contact with the filter cake. The wash step may be repeated one, two, three, or more than three times. The mother liquor and the solvent washes may be combined and the solvent may be recovered. The resultant residue may be combined with the aqueous phases described above and then subjected to the recycle process described below in section (I)(f).

The filtered crystallization product may be dried at a temperature of less than about 50° C., less than about 45° C., less than about 40° C., or less than about 35° at atmospheric pressure or under vacuum in a continuous or batchwise fashion. Suitable dryers include but not limited to a thermoventuri dryer, fluid bed dryer, tray dryer, rotary tray dryer, rotary vacuum dryer, or other suitable dryer known in the art.

The recovered crystals of the compound of Formula (II) may have a purity level of greater than about 85%, greater than about 90%, greater than about 95%, greater than about 98%, or greater than about 99%. The molar yield of the crystals of the compound of Formula (III) may be at least about 5%, at least about 10%, at least about 12%, at least about 14%, at least about 16%, at least about 18%, at least about 20%, at least about 25%, at least about 30%, at least about 35%, at least about 40%, at least about 45%, at least about 50%, at least about 60%, at least about 70%, or more than 70%.

(f) Recycle Step

In some embodiments, the processes disclosed herein further comprise a recycle step. As mentioned above, oligomers of the compounds of Formulas (I) and (II) are produced as by-products during the reaction step of the process. The monomers and oligomers of the compounds of Formulas (I) and (II) are partitioned to the aqueous phase during the phase partitioning and extraction steps of the process, are present in the water wash of the combined organic phases, and are present in the mother liquid and solvent washes generated during the crystallization step.

The recycle step of the process comprises combining the aqueous phase, the water wash, and the crystallization residue to form a monomer/oligomer mixture and hydrolyzing the oligomers in the mixture to monomers of the compounds of Formulas (I) and (II). In general, the hydrolysis is performed in a closed system under pressure at a temperature ranging from about 80° C. to about 300° C. with a preferred range of about 80° C. to about 125° C. for about 1 hour to about 6 hours. The heating may be conducted with or without an added catalyst. In some embodiments, the hydrolysis may be conducted in the presence of an acid catalyst. Suitable acid catalysts are listed above in section (I)(b). In other embodiments, the hydrolysis may be conducted in the presence of a base catalyst, examples of which are well known in the art. Following acid or base hydrolysis, the hydrolyzed oligomer mixture may be neutralized. The duration of the hydrolysis step can and will vary depending upon the concentration of the oligomers, the presence and/or concentration of the catalyst, the temperature, and the like.

The recycle step further comprises recycling the hydrolysis mixture, which comprises hydrolyzed oligomers and monomers of the compounds of Formulas (I) and (II), back to the initial reaction chamber in which the condensation reaction (detailed in section (Ib) above) takes place. In some embodiments, the recycling may be continuous. In other embodiments, the recycling may be batch-wise.

(II) Applications

The cyclic dimer compounds of Formula (III) prepared by the processes detailed above in section (I) may be used in a variety of applications. In some embodiments, the compounds of Formula (III) may be used as plasticizers, wetting agents, emulsifiers, additives, processing aids, nutritive agents, antioxidant agents, antimicrobial agents, anticorrosive agents, and feed additives. In other embodiments, the compounds of Formula (III) may be used to prepare homopolymers and copolymers as described in U.S. Pat. Nos. 9,284,294, and 9,011,832, the disclosures of which are incorporated by reference herein.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The compounds described herein have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "about," particularly in reference to a given quantity, is meant to encompass deviations of minus five percent.

The term "acyl," as used herein alone or as part of another group, denotes the moiety formed by removal of the hydroxyl group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkoxide" or "alkoxy" as used herein is the conjugate base of an alcohol. The alcohol may be straight chain, branched, cyclic, and includes aryloxy compounds.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The term "copolymer" refers to a polymer containing two or more different repeat units.

The terms "halogen" or "halo" as used herein alone or as part of another group refer to chlorine, bromine, fluorine, and iodine.

The term "heteroatom" refers to atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The term "homopolymer" refers to a polymer containing a single type of repeat unit.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

Having described the invention in detail, it will be apparent that modifications and variations are possible without departing from the scope of the invention defined in the appended claims.

EXAMPLES

The following examples illustrate various embodiments of the invention.

Example 1: Preparation of 3,6-Bis(2-methylthio)ethyl-1,4-Dioxane-2,5-Dione

A 2-L jacketed reactor was equipped with an overhead stirrer, a thermocouple, a materials addition port, a Dean Stark distillation adaptor, and a condenser. The condenser temperature was set −4° C. To the reactor was added 600 g of ALIMET® (~88% HMTBA and ~12% water), 900 g of toluene, and 3.6 g of p-toluenesulfonic acid. The mixture was stirred at 300 rpm and the reactor was sealed (with nitrogen flowing at 0.5 lpm). The jacket temperature was increased about 90° C./hour to reach a target internal reflux temperature of 112.3° C. Initially, the reaction mixture was biphasic, but became homogeneous at about 100-106° C. Once the internal temperature reached 110° C., the reaction was continued for 4 hours. The progress of the reaction was monitored by HPLC every 2 hours. Once the reaction was deemed complete, the mixture was cooled to room temperature and filtered through a glass funnel fitted with a coarse frit. To the filtrate was added 90 g of deionized water, and the mixture was stirred at 400 rpm for 5 minutes. The phases were separated and the aqueous phase was extracted twice with 810 g of toluene (the mixture was stirred at 400 rpm for 5 minutes). All three organic phases were combined and washed with 150 g of water (stirred at 100 rpm for 5 minutes).

The toluene was removed from the combined organic phases by distillation at about 40° C. or less and at about 20-30 mbar of pressure. The distillation was continued until the amount of toluene was less than 2%. To the resultant clear, orange colored liquid was added isopropanol (2 g per g of oil). The mixture was stirred at 300 rpm and heated to 35±5° C. until all of the solid material had dissolved. The stirring rate was reduced to 150 rpm and the solution was slowly cooled to about 30° C. and the solution was held at 30° C. for 3 hours. The solution was cooled to 0° C. over a period of about 2.5 hours by reducing the temperature at a rate of about 0.1° C./min for one hour and then at a rate of about 0.2° C./min until the target temperature of 0° C. was reached. Crystallization started at about 27-29° C. The product was filtered using a fritted funnel. The filter cake was slurried with 100 mL of 4° C. isopropanol for about 1 minute, and then filtered again. The re-slurry step was repeated two times. The filter cake was dried in a vacuum oven at 40° C. overnight. The final product was analyzed by HPLC. The purity was 98% or greater and the molar yield was 12-13%.

Example 2: Preparation of 3,6-Bis(2-methylthio)ethyl-1,4-Dioxane-2,5-Dione with a Recycle Step Reaction.

A 1000 mL four neck round bottom flask was equipped with a stir bar, a Dean-Stark trap filled with toluene, a thermocouple, and an $N_2$ link attached to a condenser. To the flask was added 200.05 g of ALIMET® (~88% HMTBA and ~12% water), 300 g of toluene, and 1.2255 g of p-toluenesulfonic acid (pTSA). The temperature of the reaction was set at 112° C. with the thermocouple monitoring the reaction mixture to ensure a sufficient refluxing of toluene to remove water. The reaction mixture began to boil/reflux around 89-95° C. The temperature continued to slowly rise to 110° C. at which the reaction mixture turned homogeneous and the reaction flask was thermostated at 112° C. The reaction was run for about 5 hours and sampled every hour. A typical kinetic curve is shown in FIG. 1. The yield of the cyclic dimer compound reached about 20 area % by about 4-5 hr. Once the process was deemed complete, approximately 33.55 g of water had been collected. The reaction mixture was cooled down to room temperature overnight and filtered to collect about approximately 0.2-1 gram of salts.

Phase Partitioning.

The reaction mixture (444.01 g) was transferred to a 1 L separatory funnel and mixed with 30.44 g of DI water by vigorously shaking. The layers, i.e., top layer (TL) and bottom layer (BL), were allowed to separate for 3-5 minutes. Each layer was drained and weighed (BL+$H_2O$=206.47 g and TL=263.13 g). Both of the layers were sampled for HPLC. The top (organic) layer was transferred to a 1 L Erlenmeyer flask.

Extractions.

The bottom aqueous layer from the phase partitioning step was transferred back to the separatory funnel and mixed well with 270 grams of toluene. Top and bottom layers were allowed to separate for 3-5 minutes. Each layer was drained and weighed (BL+$H_2O$=182.88 g and TL=283.89 g). Both of the layers were sampled for HPLC. The top organic layer was combined with the first organic layer in the 1 L Erlenmeyer flask.

The bottom aqueous layer from the extraction was transferred back to the separatory funnel and mixed well with another 270 grams of toluene. The layers were allowed to separate for 3-5 min. Each layer was drained and weighed (BL+$H_2O$=173.01 g and TL=281.51 g). Both of the layers were sampled for HPLC. The top layer was combined with the other organic layers in the 1 L Erlenmeyer flask. The final aqueous layer was reserved for oligomer hydrolysis and recycling (see below).

The combined top organic layer (828.53 g, clear, yellowish) was further washed with 100.81 g of DI water in a separatory funnel and separated. The bottom water layer was drained (101.99 g) and combined with the reserved bottom aqueous layer. The washed organic layer comprising the product in toluene (821.64 g) was collected into a 2 L round bottom flask (cloudy, yellowish).

Crystallization.

The round bottom flask containing 821.6 g of the washed organic layer was placed on a rotary evaporator. The water bath temperature was set to 40° C., and the vacuum pressure was initially set at 250 mbar and then slowly decreased to 30 mbar over 30 minutes. 43.57 g of crude product was obtained and fully dissolved in 65.25 g of MTBE, which was transferred to a 200 mL glass beaker that was placed in an ice bath. Crystals formed normally within 1 hour (e.g., 10-60 min). It was found that a seed of the product could help crystallization. The crystallization was allowed to proceed overnight at 4° C. The final crystals were collected by filtration (fritted glass funnel) and washed with chilled MTBE (30-40 ml). The crystals were dried at 40° C. in a vacuum oven to yield 16.30 grams of final product, 97.67% by HPLC.

Hydrolysis of Oligomers.

To a Parr reactor vessel was charged 167.90 g of the reserved aqueous layer/water wash. The vessel was tightly sealed and then heated. The mixture was stirred by a mechanical overhead stirrer at ~300 rpm. The reaction temperature was set at 125° C. (once the temperature reached about 121° C., the temperature was set at 123° C.). It took about 20 min to reach a temperature of 115-118° C., which was noted as time 0. The pressure was recorded 43 psi. The reaction was heated at 120° C. for 3 hours, and then cooled down by turning off and removing the heating mantle. Once the temperature reached 35° C., which took about 90 minutes, the pressure gauge was slowly opened to release the pressure from the vessel. Some mixture was released due to the built-up pressure in the vessel. Once the gauge was fully opened, the vessel was opened and removed from the reactor. The final weight of the hydrolyzed oligomers was recorded to be 165.52 g. It was noticed that there was a clear layer on top of the solution which was assumed to be toluene insoluble with recycled monomer. A representative aliquot of the mixture (by vigorously stirring) was taken for HPLC to calculate the amount of recycled monomer and recycled pTSA in the mixture using calibration curves. The recycled monomer and pTSA data are summarized in Table 1. All of the major peaks were identified by LC-MS to be monomer pTSA, monomer, dimer, trimer, and tetramer. There were some other minor uncharacterized impurities.

TABLE 1

Composition of Aqueous Phases Before and After Hydrolysis

|  | Monomer % | Dimer % | Trimer % | Mass g | Estimated Recovery |
|---|---|---|---|---|---|
| Before hydrolysis | 18.3 | 27.0 + 2.3(cyclic dimer) | 48.5 | 173 |  |
| After hydrolysis | 75.7 | 16.6 | 3.0 + 0.5(tetramer) | 124.1 | 62% |
| Recycled pTSA |  |  |  | 1.1 | 90% |

Reaction Using Recycled Monomer.

Figure 2:
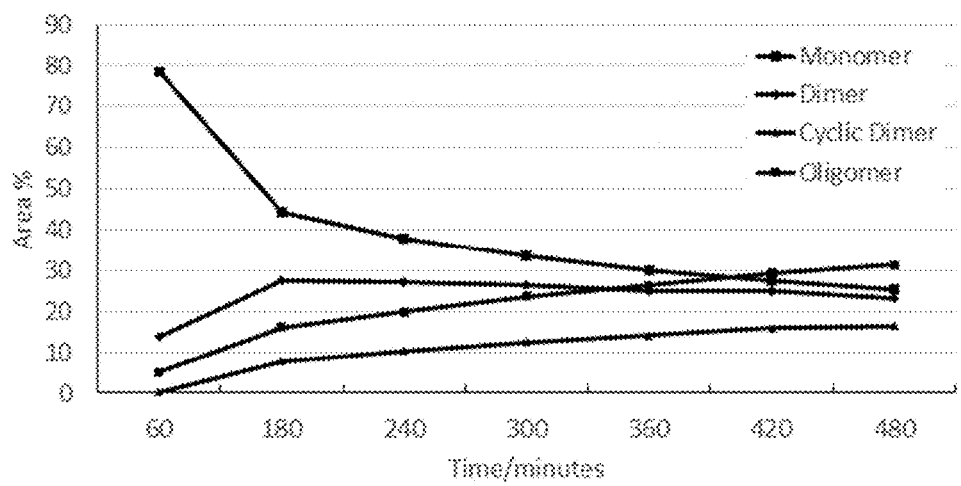
FIG. 2 shows a reaction kinetic curve using recycled monomers. The reaction components are plotted over time.

The recycled monomers were converted to the cyclic dimer using the reaction conditions detailed above, except the reaction mixture contained 0.6 wt % pTSA and 0.5 wt % sulfuric acid. A typical reaction curve using recycled HMTBA is shown in FIG. 2. Longer reaction times are needed when the reaction mixture comprises recycled monomer (which may be due to the presence of additional water in the mixture).

What is claimed is:

1. A process for preparing a compound of Formula (III) by contacting a compound of Formula (I) with a compound of Formula (II), the process comprising:
   (a) forming a reaction mixture comprising a nonpolar solvent and the compounds of Formula (I) and Formula (II), the reaction mixture comprising a weight-to-weight ratio of the nonpolar solvent to the compounds of Formula (I) and Formula (II) of less than 20:1;
   (b) heating the reaction mixture in the presence of at least one acid catalyst under dehydration to form the compound of Formula (III);
   (c) adding water to the reaction mixture after step (b) to form an aqueous phase and an organic phase comprising the compound of Formula (III), wherein the aqueous phase comprises oligomers of the compounds of Formula (I) and Formula (II) and a residual level of the compound of Formula (III);
   (d) extracting the aqueous phase with the nonpolar solvent to form another organic phase comprising the compound of Formula (III), wherein the nonpolar solvent used in step (d) is the same nonpolar solvent as that used in step (a); and (e) combining the organic phases comprising the compound of Formula (III) from steps (c) and (d), and isolating the compound of Formula (III) from the organic phases;

the compounds of Formulas (III), (II), and (I) having the following structures:

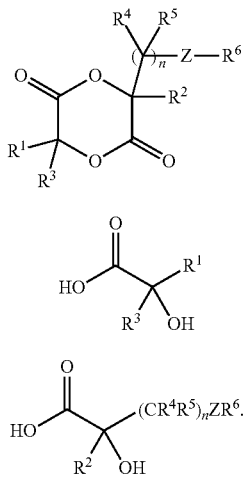

wherein:

$R^1$, $R^2$, $R^3$, $R^4$, and $R^5$ independently are hydrogen, alkyl, or substituted alkyl;

$R^6$ is hydrogen, alkyl, substituted alkyl, aryl, or substituted aryl;

Z is sulfur, sulfone, sulfoxide, or selenium; and n is an integer from 1 to 10.

2. The process of claim 1, wherein $R^2$, $R^3$, $R^4$, and $R^5$ are hydrogen, and $R^6$ is $C_1$-$C_6$ alkyl.

3. The process of claim 1, wherein $R^1$ is $(CR^8R^9)_m YR^{10}$, wherein:

$R^8$ and $R^9$ independently are hydrogen, alkyl, or substituted alkyl;

$R^{10}$ is hydrogen, alkyl, substituted alkyl, aryl, or substituted aryl;

Y is sulfur, sulfone, sulfoxide, or selenium; and m is an integer from 1 to 10.

4. The process of claim 3, wherein $R^2$, $R^3$, $R^4$, $R^5$, $R^8$, and $R^9$ are hydrogen, and each of $R^6$ and $R^{10}$ independently is $C_1$-$C_6$ alkyl.

5. The process of claim 4, wherein each of $R^6$ and $R^{10}$ is methyl, each of n and m is 2, and each of Z and Y is sulfur or selenium.

6. The process of claim 5, wherein the compound of Formula (III) is a compound of Formula (V) and each of the compounds of Formula (I) and Formula (II) is a compound of Formula (IV):

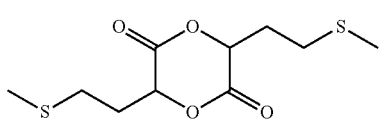

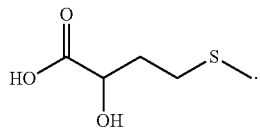

7. The process of claim 1, wherein the nonpolar solvent used in steps (a) and (d) is anisole, benzene, chlorobenzene, di-tert-butyl ether, diethylene glycol, diglyme, diisopropyl ether, ethyl tert-butyl ether, fluorobenzene, methyl tert-butyl ether, toluene, xylene, or a combination thereof.

8. The process of claim 7, wherein the nonpolar solvent is toluene.

9. The process of claim 1, wherein the weight-to-weight ratio of the nonpolar solvent to the compounds of Formula (I) and Formula (II) at step (a) is less than 10:1.

10. The process of claim 9, wherein the weight-to-weight ratio is less than 5:1.

11. The process of claim 10, wherein the weight-to-weight ratio is less than 2.5:1.

12. The process of claim 11, wherein the weight-to-weight ratio is less than 1.5:1.

13. The process of claim 1, wherein the at least one acid catalyst at step (b) is para-toluenesulfonic acid, sulfuric acid, hydrochloric acid, sodium bisulfate, ammonium bisulfate, or a combination thereof.

14. The process of claim 13, wherein the at least one acid catalyst is para-toluenesulfonic acid, sulfuric acid, or a combination thereof.

15. The process of claim 1, wherein the at least one acid catalyst at step (b) is present at a weight percent (wt %) of the acid catalyst to the compounds of Formula (I) and Formula (II) of about 0.1 wt % to about 5 wt %.

16. The process of claim 1, wherein step (b) is conducted at a temperature of about 90° C. to about 150° C.; and dehydration at step (b) comprises a distillation process.

17. The process of claim 1, wherein step (c) comprises adding water at a weight percent (wt %) of water to the reaction mix of about 2 wt % to about 20 wt %.

18. The process of claim 1, wherein the nonpolar solvent at step (d) is present at a weight-to-weight ratio of the nonpolar solvent to the aqueous phase of about 1:1 to about 2:1.

19. The process of claim 1, wherein the extracting at step (d) is continuous or is repeated a plurality of times.

20. The process of claim 1, wherein the isolating at step (e) comprises removing the nonpolar solvent from the organic phase to form a concentrate, contacting the concentrate with a solvent at a reduced temperature to form crystals of the compound of Formula (III), and isolating crystals of the compound of Formula (III).

21. The process of claim 20, wherein the solvent is isopropanol, methyl-tert-butyl ether, benzene, toluene, or combination thereof.

22. The process of claim 1, wherein, after step (d), the aqueous phase is heated in a closed system under pressure at a temperature of about 80° C. to about 125° C. such that oligomers of the compounds of Formula (I) and Formula (II) are hydrolyzed into the compounds of Formula (I) and Formula (II).

23. The process of claim 22, wherein the process further comprises recycling the compounds of Formula (I) and Formula (II) to step (a).

24. The process of claim 23, where the recycling is continuous.

25. The process of claim 1, wherein the nonpolar solvent at steps (a) and (d) is toluene, and the at least one acid catalyst at step (b) is para-toluenesulfonic acid or a combination of para-toluenesulfonic acid and sulfuric acid.

26. The process of claim 25, wherein para-toluenesulfonic acid is present at about 0.6 wt % to about 2 wt % of para-toluenesulfonic acid to the compounds of Formula (I) and Formula (II), and sulfuric acid, when present, is present at about 0.5 wt % to about 1 wt % of sulfuric acid to the compounds of Formula (I) and Formula (II).

27. The process of claim 26, wherein the isolating at step (e) comprises removing the nonpolar solvent from the organic phase to form a concentrate, contacting the concentrate with a solvent at a reduced temperature to form crystals of the compound of Formula (III), and isolating crystals of the compound of Formula (III).

28. The process of claim 27, wherein, after step (d), the aqueous phase is heated in a closed system under pressure at a temperature of about 80° C. to about 125° C. such that oligomers of the compounds of Formula (I) and Formula (II) are hydrolyzed into the compounds of Formula (I) and Formula (II), and the process further comprises recycling the compounds of Formula (I) and Formula (II) to step (a).

* * * * *